United States Patent [19]
Spencer et al.

[11] Patent Number: 5,916,569
[45] Date of Patent: Jun. 29, 1999

[54] HUMAN ERECTILE DYSFUNCTION AND METHODS OF TREATMENT

[75] Inventors: E. Martin Spencer, 505 Ortega St., San Francisco, Calif. 94122; Thomas Lue, Hillsborough, Calif.

[73] Assignee: E. Martin Spencer, San Francisco, Calif.

[21] Appl. No.: 08/824,523

[22] Filed: Mar. 26, 1997

[51] Int. Cl.$^6$ .......................... A61K 39/00; A61K 38/00
[52] U.S. Cl. .......................... 424/198.1; 514/2; 930/120
[58] Field of Search .................. 514/2, 866, 21; 930/120; 424/198.1

[56] References Cited

U.S. PATENT DOCUMENTS

| | | | |
|---|---|---|---|
| 4,988,675 | 1/1991 | Froesch et al. | 514/4 |
| 5,068,224 | 11/1991 | Fryklund et al. | 514/21 |
| 5,447,912 | 9/1995 | Gerstenberg et al. | 514/12 |

OTHER PUBLICATIONS

Tom F. Lue, M.D. "Physiology of Erection and Pathophysiology of Impotence", *Sexual Function*, 6th Ed., (1992) pp. 709–727.

Skottner, A. et al. "Anabolic and tissue Repair Functions of Recombinant Insulin–Like Growth Factor I", *Acta Paediatr Scand*, Suppl. 367, (1990) pp. 63–66.

Martin, Human Growth Hormone, Eds. Raiti and Tolman, Plenum Publishing Corporation, NY, NY, pp. 303–323, 1986.

Hintz, Human Growth Hormone, Eds. Raiti and Tolman, Plenum Publishing Corporation, NY, NY, pp. 553–561, 1986.

*Primary Examiner*—Jon P. Weber
*Assistant Examiner*—Janet M. Kerr
*Attorney, Agent, or Firm*—David J. Weitz; Wilson Sonsini Goodrich & Rosati

[57] ABSTRACT

This invention is a method for treating human erectile dysfunction using therapeutic amounts of human growth hormone (GH) administered systemically. Severing the parasympathetic nerves that regulate the erectile function during the course of surgery produces erectile dysfunction. Damage to these nerves by diseases such as diabetes mellitus and alcoholism and during aging may also produce erectile dysfunction. GH stimulates the regeneration of severed parasympathetic nerves that regulate the erectile function restoring potency. GH may act directly or by stimulating the production of insulin-like growth factor-I (IGF-I). The combination of GH plus an IGF (with or without one of the IGF binding proteins) may provide a better response than GH alone.

12 Claims, No Drawings

HUMAN ERECTILE DYSFUNCTION AND METHODS OF TREATMENT

FIELD OF THE INVENTION

This invention relates to human erectile dysfunction (male impotence) and methods to treat this condition.

BACKGROUND

Physiology of the Erectile Response

The engorgement of two erectile bodies in the penis (corpora cavernosa) with blood produces the erection. An erection occurs when parasympathetic nervous impulses simultaneously relax the arterial supply to the corpora and the smooth muscle cells in the corpora allowing blood to flow into the sinuses (spaces) of the corpora. Engorgement with blood compresses the venous outflow against the rigid fibrous membrane (tunica albuginea) around the corpora trapping the blood within the erectile bodies producing the erection.

Etiology of Erectile Dysfunction

Erectile dysfunction is defined as the inability to achieve an erection sufficient for intercourse. The cause of erectile dysfunction (impotence) can be defined by diagnostic modalities, such as color duplex sonography, administration of vasoactive agents into one of the two corpora cavernosa (the erectile bodies in the penis), nocturnal penile tumescence testing, and measurement of the pressure in the cavernosa (cavernosometry) Lue, T. F. and Tanagho, E. A., "Physiology of erection and pharmacologic management of impotence," *J. Urol.* 137, pp 829–832, (1987). Erectile dysfunction can be defined as (1) psychogenic, (2) neurogenic, (3) hormonal, (4) vascular, (5) cavernosal, (6) drug induced or (7) a combination of these etiologic elements. The majority of patients with erectile dysfunction suffer from aging changes of the neurovascular supply of the penis and the pelvic ganglia. Lue T. F., "Physiology of penile erection and pathophysiology of impotence," in *Campbell's Urology*, Sixth Edition, eds. Walsh P. C. et al. (W. B. Saunders 1992) pp. 707–728.

Therapy Lue T. F., "Physiology of penile erection and pathophysiology of impotence," in *Campbell's Urology*, Sixth Edition, eds. Walsh P. C. et al. (W. B. Saunders 1992) pp. 707–728. Psychosexual therapy or counseling is the preferred treatment for patients with psychogenic erectile dysfunction. Testosterone replacement is effective for patients with testosterone deficiency. Change or discontinuing offending medications or illicit drugs may help the appropriate patients. Oral or topical medications for erectile dysfunction have not been very helpful. Intraurethral alprostadil provides some, but not complete improvement of the erectile response in approximately 50% of patients. The penile prostheses include a wide array of implantable, commandable and near-physiologic devices to permit intercourse. Self-injection into the cavernosa uses several agents such as papaverine, phentolamine and alprostadil, or a combination of drugs. Vacuum and compression devices provide additional options to the patient and physician. Arterial reconstruction and venous surgery are effective only for young patients with localized vascular problems. No effort has been made to stimulate nerve regeneration as a way to prevent or cure impotence.

The treatments described above may help the patient to achieve a better erection and an erection which will, temporarily, last longer. Except for penile revascularization and testosterone replacement, other current impotence treatments are non-specific and do not offer a cure or prevention. Unfortunately, only a very small number of patients suffer from hormonal deficiency or a curable penile vascular disease. Therefore, the vast majority of patients require either a permanent penile implant or treatment prior to sexual intercourse with intracavernous injection, intraurethral injection, or a vacuum device. Since there are drawbacks to all these therapies, most patients have not availed themselves of treatment. Therefore, a more physiologic approach to either prevent or cure erectile dysfunction is highly desirable. To date no one has successfully addressed restoration of potency secondary to radical pelvic surgery for prostatic and urinary bladder cancer and other surgeries that may damage the pelvic parasympathetic innervation of the penis such as vascular and colo-rectal surgery.

Growth Hormone

Human growth hormone (also referred to as somatotropin and "GH") is a growth-promoting, anabolic polypeptide hormone of approximately 21,400 daltons. Jameson, J. L., "Growth Hormone" in *Cecil Textbook Of Medicine*, eds. Bennett, J. C. and Plum, F. (W. B. Saunders 1996) pp.1210–1212. GH is synthesized in the pituitary gland and released into the circulation. Some of the GH circulating in plasma is bound to a binding protein which in humans is the extracellular domain of the cell surface GH receptor. The plasma level of GH can be determined by radioimmunoassay, ELISA, or radioreceptor assay. GH secretion is regulated positively and negatively by peptides released from the hypothalmus, GH releasing factor (GHRF) and somatotropin release inhibiting factor (SRIF), respectively, and is feedback inhibited by insulin-like growth factor-I (also referred to as somatomedin-C and IGF-I).

GH stimulates: a) human and other animal growth, b) the growth of various organs and tissues in the body that include skeletal tissues, c) the synthesis of IGF-I, d) cellular amino acid uptake and protein synthesis (while decreasing protein degradation), e) wound healing in elderly healthy subjects, f) immune functions, g) lipolysis (the breakdown of fat), h) the secretion of insulin, and i) the resistance of tissues to insulin. Papadakis, M. A. et al., "Effect Of Growth Hormone Replacement On Wound Healing In Healthy Older Men," *Wound Rep. Reg.* 4, p 421 (1996). GH has not been reported to stimulate parasympathetic nerve regeneration.

IGF-I mediates many of the growth-promoting effects of GH on tissues and mediates many of the anabolic actions of GH. Schlechter, N. L. et al., "Evidence Suggesting That The Direct Growth-promoting Effect Of Growth Hormone On Cartilage in vivo Is Mediated By Local Production Of Somatomedin," *Proc. Natl. Acad. Sciences* 83, p. 7932 (1986). IGF-I has a quantitatively different degree of action than GH on certain tissues and has an additive effect on body growth when administered with GH in vivo in animals deficient in GH. Fielder, P. J. et al., "Differential Long-term Effects Of Insulin-like Growth Factor-I (IGF-I) Growth Hormone (GH), And IGF-I plus GH On Body Growth And IGF Binding Proteins In Hypophysectomized Rats," *Endocrinology* 137, p. 1913 (1996). IGF-I has been reported to stimulate guanylyl cyclase to increase tissue levels of cGMP in lymphocytes and chondrocytes. Spencer, E. M. et al., "The Effect Of Somatomedin On Adenylyl Cyclase And Guanylyl Cyclase Activity In Various Tissues," in *Somatomedins And Growth* eds. Giordano, G. et al., (Academic Press 1979) p 37; cGMP is known to be a mediator for smooth muscle actions involved in the erectile response.

IGF-I action is also regulated by a class of 6 circulating specific binding proteins, the most abundant being IGF binding protein-3, also known as "IGFBP-3." Shimasaki, S. et al., "Isolation And Molecular Characterization Of Three Novel Insulin-like Growth Factor Binding Proteins (IGFBP-4, 5 and 6)" in *Modern Concepts Of Insulin-Like Growth Factors,* ed. Spencer, E. M., (Elsevier, 1991) p. 343–358; Spencer, E. M. et al., "Insulin-like Growth Factor Binding Protein-3 Is Present In The α-Granules Of Platelets," *Endocrinology* 132, p. 996 (1993). After association with IGF-I, the action of IGF-I is generally inhibited by IGFBPs, but under certain conditions the complex of IGF-I with an IGFBP may be stimulatory. Sommer, A. et al., "Molecular Genetics And Actions Of Recombinant Insulin-like Growth Factor Binding Protein-3" in *Modern Concepts Of Insulin-Like Growth Factors,* ed. Spencer, E. M., (Elsevier 1991) p. 715–728. Both IGF-I and GH have been claimed to stimulate the synthesis of IGFBP-3.

GH is used therapeutically to increase the growth of GH-deficient children, to improve muscle function and well-being in GH-deficient adults, to reduce the wasting in patients with AIDS, and to speed donor-site healing in burn patients. GH has been reported to be ineffective in impotence and to produce erectile insufficiency. Ra, S. et al., "In Vitro Contraction Of The Canine Corpus Cavernosum Penis By Direct Perfusion With Prolactin Or Growth Hormone," *J. of Urology,* 156, p. 522 (1996). GH has never been investigated for its reparative effects on pelvic parasympathetic nerves damaged by surgery or other conditions known to adversely affect parasympathetic nerves such as diabetes, alcoholism and aging.

GH may be useful in vivo to prevent and/or treat erectile dysfunction that occurs after radical prostatectomy, radical cystectomy (removal of the urinary bladder) or other surgeries that may damage the pelvic parasympathetic nerves such as rectal and vascular. GH may be useful to treat other organic causes of erectile dysfunction. GH in combination with an IGF, an IGF:IGFBP complex, or another growth factor may be more efficatious in treating erectile dysfunction.

DISCLOSURE OF THE INVENTION

In this description, the following terms are employed:

Corpora Cavernosa

Two erectile bodies in the penis. Filling these with blood produces the erection.

Cavernous nerve

The nerve that supplies the small arteries and erectile tissues within the penis. It carries the impulses from the brain to the penis to produce erection. Because of its dose relation to the prostate, the cavernous nerve is often injured during prostate or bladder surgery. It also undergoes various degrees of degeneration in older men, heavy alcoholism and patients with diabetes mellitus.

Dorsal Nerve of the Penis

The nerve located under the skin of the penis. It contains both sensory nerves and branches of the cavernous nerve.

Nitric Oxide Synthase (NOS)

An enzyme the produces nitric oxide which is the principal neurotransmitter for penile erection. Histochemical staining of nitric oxide synthase is a convenient way to localize the erection nerves.

Pelvic Ganglia

A collection of the bodies of nerve cells (neurons) in the pelvis that innervate the pelvic organs such as rectum, bladder, prostate, seminal vesicle and the penis.

Intracavernous Therapy

Injection directly into one of the two erectile bodies of the penis, cavernosum, with a needle.

Intraurethral Therapy

Application of the agent into the penis through the external end of the urethra.

Intracavernous Trabeculae

The supporting structure inside the corpora cavernosa. The fibrous skeleton provides support to the smooth muscles and provides passage for the branches of the cavernous nerve and artery.

Neurotrophic Growth Factors

Factors that stimulate nerve growth such as nerve growth factor, neurotropins, brain-derived neurotrophic factor, cilliary neurotrophic factor, fibroblast growth factors, and insulin-like growth factors.

The invention solves the problem of impotence secondary to pelvic surgery, pelvic injury, alcoholism, diabetes mellitus, aging, or any condition that irreversibly damages the penile nerves. Erectile dysfunction in older men of other causes may also be improved or reversed by the treatment referred above.

In experimental studies erectile dysfunction was produced in rats by cutting one of the cavernous nerves supplying the penis. GH was administered in a dose of 300 ug/day twice daily subcutaneously for 21 days in 14 rats. When studied after 3 months and compared to placebo, GH significantly improved the number of the parasympathetic nerves and the erectile function. The erectile function was measured as intracavernous pressure during electrostimulation of the contralateral cavernous nerve. GH was shown to have a specific effect on regeneration of the nerves responsible for the erectile response. GH significantly increased the number of nitric oxide synthase (NOS) positive nerves in the intracavernous trabeculae and the dorsal nerve of the penis. Further evidence showed that these increases were due to stimulation of parasympathetic nerve fiber growth from the contralateral, unsevered penile nerves.

Since IGF-I levels were increased in the rats administered GH, it is likely that GH acts by stimulating IGF-I production. IGF-I is the mediator of many of the actions of GH and has been shown to stimulate regeneration of other types of nerves. Skottner, A. et al., "Anabolic And Tissue Repair Functions Of Recombinant Insulin-like Growth Factor I," *Acta Paediatrica Scandinavica. Supplement,* 367, p. 63 (1990). Our study is the first that shows the beneficial effect of GH on the regeneration of the erection nerves specifically the parasympathetic, nitric oxide synthase-containing cavernous and dorsal nerves. Combination of GH with IGF-I (with or without an IGFBP) may give a heightened response in view of their additive effects on growth of certain organs and body weight in rats. Combination of GH with other growth factors, neurotrophins, or cytokines may also be effective. Therapy will be given by the most effective mode as is systemically, intracavernously or intraurethrally, and for the most effective duration.

BEST MODE OF CARRYING OUT THE INVENTION

Administer GH systemically in a therapeutic concentration daily for a) 30 to 90 days or b) an effective course to be determined post radical prostate surgery, after any pelvic surgery or injury that damages the innervation of the erectile response, or once the cause of impotence is determined.

What is claimed is:

1. A method for treating erectile dysfunction comprising systemically delivering to a patient whose parasympathetic nerves which regulate erectile function have been damaged or severed an effective amount of insulin-like growth factor-I.

2. The method of claim 1, wherein the systemic delivery occurs over a plurality of days.

3. The method of claim 2, wherein the plurality of days is at least 30 days.

4. The method of claim 2, wherein the plurality of days is between about 30 and 90 days.

5. A method for treating erectile dysfunction comprising systemically delivering to a patient whose parasympathetic nerves which regulate erectile function have been damaged or severed an effective amount of a composition which stimulates production in the patient of insulin-like growth factor-I.

6. The method of claim 5, wherein the systemic delivery occurs over a plurality of days.

7. The method of claim 6, wherein the plurality of days is at least 30 days.

8. The method of claim 6, wherein the plurality of days is between about 30 and 90 days.

9. A method for treating erectile dysfunction comprising systemically delivering to a patient whose parasympathetic nerves which regulate erectile function have been damaged or severed an effective amount of human growth hormone which stimulates production in the patient of insulin-like growth factor-I.

10. The method of claim 9, wherein the systemic delivery occurs over a plurality of days.

11. The method of claim 10, wherein the plurality of days is at least 30 days.

12. The method of claim 10, wherein the plurality of days is between about 30 and 90 days.

* * * * *